(12) United States Patent
Vikström et al.

(10) Patent No.: US 9,746,850 B2
(45) Date of Patent: Aug. 29, 2017

(54) COMPUTER-IMPLEMENTED SYSTEMS AND METHODS FOR GENERATING GENERALIZED FRACTIONAL DESIGNS

(71) Applicant: MKS Instruments, Inc., Andover, MA (US)

(72) Inventors: Ludvig Vikström, Umeå (SE); Conny Vikström, Umeå (SE); Erik Johansson, Umeå (SE); Gustaf Hector, Göteborg (SE)

(73) Assignee: Sartorius Stedim Biotech GmbH, Goettingen (DE)

(*) Notice: Subject to any disclaimer, the term of this patent is extended or adjusted under 35 U.S.C. 154(b) by 707 days.

(21) Appl. No.: 14/273,669

(22) Filed: May 9, 2014

(65) Prior Publication Data
US 2015/0323512 A1 Nov. 12, 2015

(51) Int. Cl.
*G06F 19/00* (2011.01)
*G05B 23/02* (2006.01)
*G01N 33/15* (2006.01)

(52) U.S. Cl.
CPC ........ *G05B 23/021* (2013.01); *G01N 33/15* (2013.01); *G06F 19/704* (2013.01)

(58) Field of Classification Search
CPC ...... G01N 33/15; G05B 23/021; G06F 19/704
See application file for complete search history.

(56) References Cited

U.S. PATENT DOCUMENTS

| 8,938,707 B2 * | 1/2015 | Tadagalale | G06F 11/3604 705/29 |
| 2006/0057734 A1 * | 3/2006 | Chen | G01N 13/00 436/164 |

OTHER PUBLICATIONS (C1) Banerji, Shubhra, "Orthogonal Array Approach for Test Case Optimization," International Journal of Advanced Research in Computer and Communication Engineering, vol. 1 (9), Nov. 2012, pp. 613-621.
(C2) Jones, Bradley, et al., "A Class of Three-Level Designs for Definitive Screening in the Presence of Second-Order Effects," Journal of Quality Technology, vol. 43 (1), Jan. 2011, pp. 1-15.
(C3) Kuhfeld, Warren F., "Sawtooth Software—Research Paper Series—Efficient Experimental Designs Using Computerized Searches," SAS Institute, Inc. 1997, Sequim, WA, 98382, 14 pages.

* cited by examiner

*Primary Examiner* — Elias Desta
(74) *Attorney, Agent, or Firm* — Proskauer Rose LLP

(57) ABSTRACT

A method and system for creating a design plan to test a product characteristic are described. One or more factors, level corresponding to the factors, and partitions for testing the product characteristic are determined. For each partition, an active matrix is generated. The product characteristic can be tested at each partition using the levels for the factors specified by the corresponding active matrix.

25 Claims, 9 Drawing Sheets

| Example 1 | | | | | |
|---|---|---|---|---|---|
| Part./Factor | $x_1^2$ | $x_2^2$ | $x_3^3$ | $x_4^4$ | $X_5^7$ |
| 1 | {1} | {1} | {1} | {1,4} | {1,4,7} |
| 2 | {2} | {2} | {2} | {2} | {2,5} |
| 3 | {} | {} | {3} | {3} | {3,6} |

| Example 2 | | | |
|---|---|---|---|
| Set/Factor | $x_1^2$ | $x_2^3$ | $x_3^4$ |
| 1 | {1} | {1,3} | {1,3} |
| 2 | {2} | {2} | {2,4} |

Example B
$p = 3, n = 3$

| 1 | 2 | 3 | $= L^1$ |
| 3 | 1 | 2 | $= L^2$ |
| 2 | 3 | 1 | $= L^3$ |

1002

Example B, iteration 2

Out:

$A_1 = \begin{pmatrix} 1 & A_1 \\ 2 & A_2 \\ 3 & A_3 \end{pmatrix} \quad A_2 = \begin{pmatrix} 1 & A_3 \\ 2 & A_1 \\ 3 & A_2 \end{pmatrix} \quad A_3 = \begin{pmatrix} 1 & A_2 \\ 2 & A_3 \\ 3 & A_1 \end{pmatrix}$ $A_1 = \begin{pmatrix} 1 & 1 & 1 & 1 & 2 & 2 & 1 & 3 & 3 & 2 \\ 1 & 2 & 2 & 1 & 3 & 3 & 2 & 1 & 1 & 3 \\ 2 & 3 & 2 & 1 & 2 & 2 & 3 & 3 & 1 & 2 \\ 2 & 3 & 3 & 1 & 3 & 1 & 3 & 2 & 1 & 2 \\ 3 & 2 & 3 & 3 & 2 & 2 \end{pmatrix}$

1004

$A_2 = \begin{pmatrix} 1 & 1 & 3 & 1 & 2 & 1 & 1 & 2 & 3 & 2 & 3 & 1 \\ 1 & 2 & 1 & 1 & 3 & 2 & 2 & 2 & 2 & 3 & 1 & 2 & 3 \\ 2 & 3 & 2 & 1 & 2 & 1 & 3 & 1 & 2 & 3 \\ 3 & 2 & 3 & 1 \end{pmatrix}$

1006

$A_3 = \begin{pmatrix} 1 & 2 & 1 & 3 & 1 & 3 & 1 & 2 & 1 & 3 & 2 & 1 & 3 \\ 1 & 1 & 2 & 3 & 3 & 1 & 2 & 1 & 3 & 2 & 1 & 1 & 2 & 2 & 3 \\ 2 & 3 & 2 & 1 & 2 & 1 & 3 & 3 & 3 & 3 \end{pmatrix}$

1008 end

FIG. 12

COMPUTER-IMPLEMENTED SYSTEMS AND METHODS FOR GENERATING GENERALIZED FRACTIONAL DESIGNS

TECHNICAL FIELD

The invention generally relates to computer-implemented methods and apparatuses for creating a design plan to test a product characteristic.

BACKGROUND

In the pharmaceutical industry, stability testing is conducted as part of product development to test the quality of pharmaceutical formulations. Stability of a pharmaceutical product can be defined as the capability of a particular formulation in a specific container/closure system to remain within its physical, chemical, and/or microbiological specifications. In particular, stability of a pharmaceutical product determines the extent to which the product retains the expected properties from packaging and throughout its period of storage and use. Stability testing thus evaluates, often repeatedly over time, the effect of the formulation and environmental factors on the quality of the product, thereby predicting its shelf life. Other industrial sectors also use stability testing, such as the food, beverage and cosmetics industries, to evaluate product robustness over time.

Traditionally, when performing stability testing, all possible combinations of factors involved need to be tested, which necessitates a large number of experimental trials that can be costly and time-consuming. Using the biopharmaceutical industry as an example, a user can complete a stability study by testing all combinations of various factors involved in a formulation, including buffers (4 levels), pH (4 levels), preservatives (3 levels) and concentration of active pharmaceutical ingredient (API) (3 levels), thus yielding 144 trial formulations (4*4*3*3). In addition, the trials can be conducted at multiple points in time, such as at 0, 1, 3, 6, 9, 12, 18, 24 and 36 months and with two or three different analytical methods. The cost of testing each trial formulation can be from $1,000 to $5,000 USD. Therefore, the overall testing expense can be quite high, especially if all 144 trial formulations are tested at each time point with several different analytical methods.

Product characteristic testing is used in various industries, not limited to the biopharmaceutical industry. Moreover, testing can be conducted in relation to various product characteristics, including characteristics associated with the product itself, a process for developing the product, or a procedure related to the product. In general, an experimental design for testing a product characteristic can be created based on (i) one or more factors, each factor specifies a parameter for testing the product characteristic, (ii) one or more levels for each factor, where each level specifies a different setting (e.g., value) for the corresponding factor and (iii) one or more partitions (e.g., points in time) at which the testing needs to be conducted.

As an example, in the field of mass spectrometry (MS), a scientist needs to routinely optimize and adjust a MS system to deliver strong and stable signals for selected peaks and low signals for interfering peaks. Such an MS system has multiple factors, each can be adjusted at 6 to 10 different levels. At minimum, assuming there are 4 factors and each factor has 6 levels, the number of combinations to investigate per time point is 1296 (6^4). As another example, in the field of market research, responses of people in five age groups can be evaluated with respect to a variety of factors related to product advertisement, including product packaging (fancy, standard, or environmental), pricing ($10, $12, or $14 USD), and branding (generic or sophisticated). Hence, 90 trials need to be conducted to investigate all combinations of the different levels of the various factors involved. In many cases, it may not be feasible to perform all 90 trials. Therefore, 30 trials may be conducted to study the main features and their potential synergies (e.g., interactions). However, because the cost involved with conducting the 30 trials per time point is still high, there is a desire to reduce the number of trials even further while capturing the main features.

Traditional methods for reducing the number of experiments used to test a product characteristic usually only work with systems involving factors having 2 different levels. Hence, there exists a market demand for algorithms that can efficiently handle problems involving multilevel factors (i.e. factors with more than 2 levels). There are several challenges to creating such an algorithm. For example, experimental designs that provide optimal statistical conditions for a series of trials in an investigation are often of the orthogonal array type. While orthogonal arrays are relatively straightforward to apply, they can only be used in very limited cases for certain sets of factors and certain number of trial runs due to their mathematical properties. It cannot be guaranteed that for a given set of factors, levels and runs an orthogonal array can be defined and used for the purpose of creating a test plan.

SUMMARY

Therefore, there is a need for more efficient methods and systems for reducing the number of experiments required to test a product characteristic. In addition, systems and methods of the present technology can provide orthogonal or nearly orthogonal and balanced experimental designs for an application that has multilevel factors. Moreover, the experimental design at each partition can have one or more desirable properties, including orthogonality or near orthogonality and balance.

In one aspect, a computer-implemented method is provided for creating a design plan to test a product characteristic. The method includes determining, by a computing device, (i) a plurality of factors corresponding to different parameters for testing the product characteristic, (ii) a plurality of levels corresponding to different settings of each factor, and (iii) one or more partitions for testing the product characteristic. The method also includes decomposing, by the computing device, the plurality of factors to generate a plurality of level sets. Each level set comprises 0 or more levels assignable to each factor at each partition. In addition, the method includes generating, by the computing device, a plurality of orthogonal arrays by distributing elements of each matrix using at least one Latin square matrix. Each orthogonal array corresponds to a partition, and an element of each orthogonal array indexes a level set from the plurality of level sets produced from the decomposition. Furthermore, at each of the one or more partitions, the method includes mapping each row of the corresponding orthogonal array to the plurality level sets to form a combination of level sets. Each row of the orthogonal array determines the formation of the combination by specifying the level sets to combine. The plurality of combinations of level sets generated from the rows of the orthogonal array is then concatenated to form an active matrix at each partition.

Each row of the active matrix specifies a level of each of the plurality of factors for testing the product characteristic at the corresponding partition.

In another aspect, a computer-implemented system is provided for creating a design plan to test a product characteristic. The system includes a setup module, a decomposition module, an orthogonal arrays generation module, and an active matrix generation module. The setup module determines (i) a plurality of factors corresponding to different parameters for testing the product characteristic, (ii) a plurality of levels corresponding to different settings of each factor, and (iii) one or more partitions for testing the product characteristic. The decomposition module decomposes the plurality of factors to generate a plurality of level sets. Each level set comprises zero or more levels assignable to each factor at each partition. The orthogonal arrays generation module generates a plurality of orthogonal arrays by distributing elements of each matrix using at least one Latin square matrix. Each orthogonal array corresponds to a partition, and an element of each orthogonal array indexes a level set from the plurality of level sets produced by the decomposition module. The active matrix generation module generates an active matrix at each of the one or more partitions. The active matrix generation module can accomplish this by mapping each row of the corresponding orthogonal array to the plurality level sets to form a combination of level sets, where each row of the orthogonal array determines the formation of the combination by specifying the level sets to combine. In addition, the active matrix generation module can concatenate the plurality of combinations of level sets generated from the rows of the orthogonal array to form the active matrix. Each row of the active matrix specifies a level of each of the plurality of factors for testing the product characteristic at the corresponding partition.

In other examples, any of the aspects above can include one or more of the following features. In some embodiments, the one or more partitions comprise a plurality of points in time for testing the product characteristic. In some embodiments, each factor is associated with a type comprising one of a quantitative, categorical, discrete or ordinal type.

In some embodiments, the Latin square matrix is random.

In some embodiments, the product characteristic comprises a product feature, a process or a procedure. Testing of the product characteristic can be performed at each of the one or more partitions using the levels specified by the corresponding active matrix.

In some embodiments, the active matrices for the one or more partitions cover all combinations of the plurality of levels for the plurality of factors. Each active matrix can achieve orthogonality or near orthogonality. In addition, each active matrix can be balanced.

In some embodiments, each orthogonal array has a size of $p^{n-1}$ by n, where p represents the number of the one or more partitions and n represents the number of the plurality of factors. In some embodiments, each orthogonal array is reduced if a level set is an empty set with no elements. Reducing the orthogonal array can comprise removing each row in the orthogonal array that includes an element indexing to an empty set of the plurality of level sets.

In some embodiments, generating the orthogonal arrays at the one or more partitions includes the following steps: (a) determining the number of the one or more partitions p and the number of the plurality of factors n; and (b) forming a plurality of matrices $A_i$ based on a set X of cardinality p, where $i \in [1,p]$. The steps also include: (c) creating a random Latin square matrix of size p by p; and (d) augmenting each of the plurality of matrices $A_i$ based on the Latin square matrix. The steps further include (e) repeating steps c to d if the number of columns of each of the plurality of matrices $A_i$ is less than n. Each of the plurality of matrices $A_i$ represents an orthogonal array.

In some embodiments, the product characteristic represents a metric related to a pharmaceutical formulation and the plurality of factors represent parameters for testing the pharmaceutical formulation with respect to the metric. The metric can be the stability of the pharmaceutical formulation. The plurality of factors can comprise one or more of an active pharmaceutical ingredient (API) concentration, a pH level, a methionine concentration, or a temperature level. For the factor corresponding to the API concentration, the plurality of levels can be selected from within a range of 15 to 20 mg/ml. For the factor corresponding to the pH level, the plurality of levels can be selected from within a range of 5.5 to 6.5. For the factor corresponding to the methionine concentration, the plurality of levels can be selected from within a range of 5 to 15 mM. For the factor corresponding to the temperature level, the plurality of levels can be selected from within a range of 5 to 25 C. The one or more partitions can comprise a plurality of points in time selected from within a range of 0 to 36 months.

Some implementations include any of the above-described aspects featuring any of the above embodiments or benefits thereof.

These and other features will be more fully understood by reference to the following description and drawings, which are illustrative and not necessarily to scale. Although the concepts are described herein with respect to a manufacturing process, particularly a pharmaceutical process, it will be apparent to one of skill in the art that the concepts have additional applications, for example, pharmaceutical or biotechnical applications, metallurgic and mining applications, financial data analysis applications, or other applications involving a large number of data points or observations.

BRIEF DESCRIPTION OF THE DRAWINGS

The foregoing and other objects, features and advantages will be apparent from the following more particular description of the embodiments, as illustrated in the accompanying drawings in which like reference characters refer to the same parts throughout the different views. The drawings are not necessarily to scale, emphasis instead being placed upon illustrating the principles of the embodiments.

FIG. 3 shows exemplary level sets generated using the method of FIG. 2.

FIG. 4 shows exemplary orthogonal arrays generated using the method of FIG. 2.

FIG. 12 shows another set of exemplary Latin square matrix and augmented $A_i$ matrices created by the method of FIG. 7 during a second iteration.

DETAILED DESCRIPTION

Figure 1:
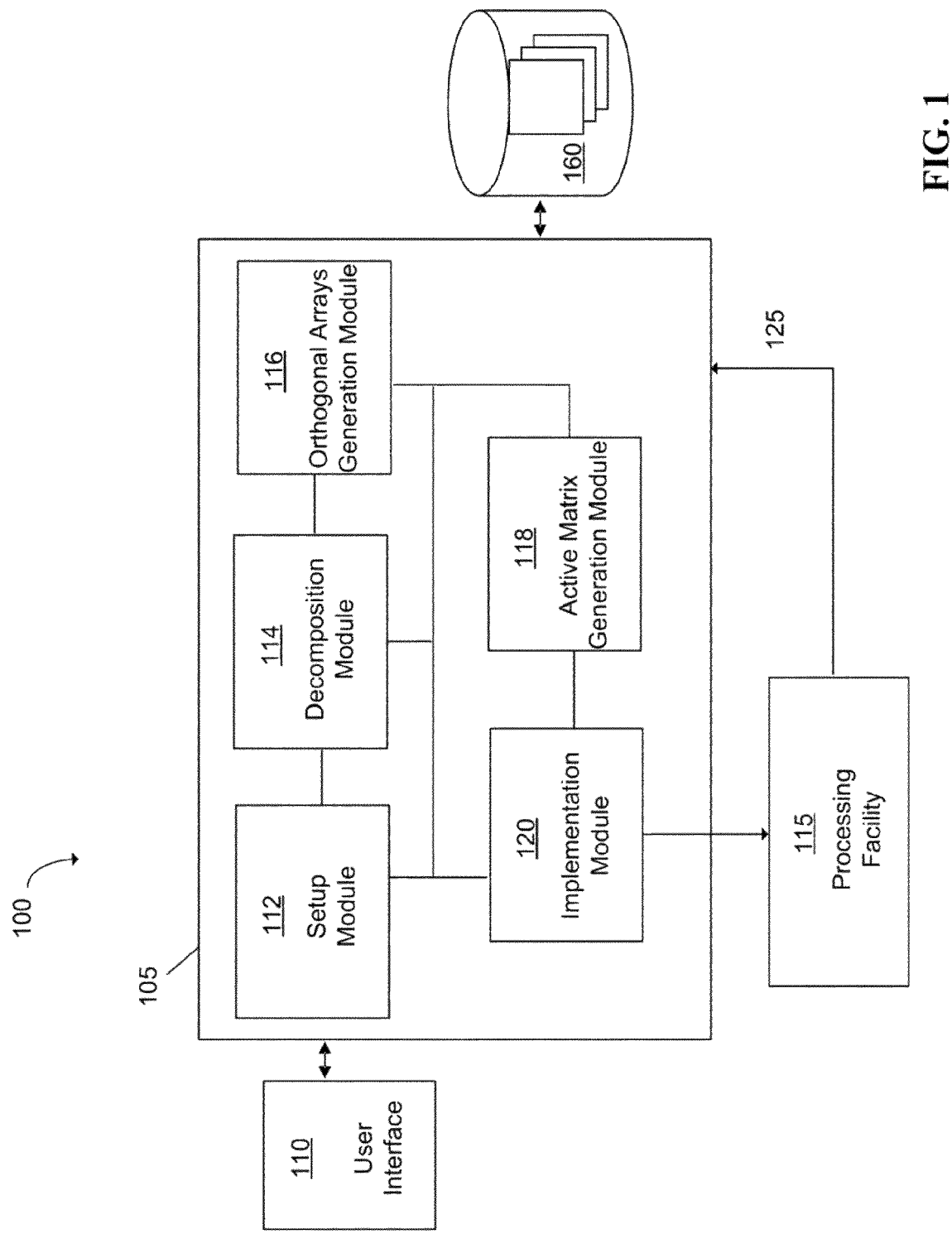
FIG. 1 shows an exemplary block diagram of a testing system.

FIG. 1 shows an exemplary block diagram of a testing system 100 that includes a processor 105 and a user interface 110. The user interface 110 can include a computer keyboard, mouse, other haptic interfaces, a graphical user interface, voice input, or other input/output channel for a user to communicate with the processor 105 in response to stimuli from the processor 105 (e.g., to specify settings for factors). The user interface 110 can include a display such as a computer monitor. The processor 105 is coupled to a processing facility 115 that automates or directs testing with respect to a characteristic of a product. For example, in the context of the biopharmaceutical industry, the processing facility 115 can perform processing functions on a formulation to determine the stability of the formulation. Testing the stability of a biopharmaceutical formulation is illustrative only, and can be representative of any measurable product characteristic. The processing facility 115 can include tools or processes (not shown) for performing tasks pertinent to the testing process (e.g., assay units and chemical metering systems).

Testing can be done in accordance with a design plan generated by the processor 105 that assigns levels to various factors for testing the product characteristic at each partition (e.g., point in time). For example, the processor 105 can specify a level for a buffer, a pH, a preservative and/or an API concentration at each partition of the testing process to determine the stability of a formulation. In addition, an output 125 of the processing facility 115 (e.g., a stability measurement of the formulation) in response to the testing can be monitored over the span of one or more partitions and can be used by the processor 105 to predict future stability behavior.

As shown in FIG. 1, the processor 105 includes several modules, including a setup module 112, a decomposition module 114, an orthogonal arrays generation module 116, an active matrix generation module 118 and optionally, an implementation module 120. The modules can be implemented in hardware only or in a combination of hardware and software to execute the processes described below with reference to FIGS. 2 and 7.

In particular, the setup module 112 is configured to receive and process data from the user interface 110, including (i) a description of the product characteristic being tested, (ii) one or more factors supplied by a user to specify different parameters/variables for testing the product characteristic, (iii) one or more levels defining different possible settings (e.g., values) of each factor, and (iv) one or more partitions (e.g., points in time). In general, the data can be provided by the user interface 110 and/or processed by the setup module 112 as data structure(s) such as, for example, textual lists, XML documents, class objects (e.g., instances of C++ or Java classes), other data structures, or any combination thereof.

The decomposition module 114 is configured to decompose the levels of the factors from the setup module 112 to generate one or more level sets for each partition, where each level set includes zero or more levels assignable to each factor at the corresponding partition. The orthogonal arrays generation module 116 is configured to generate an orthogonal array for each partition. Elements of each orthogonal array correlate to a level set produced by the decomposition module 114. The active matrix generation module 118 is configured to generate an active matrix at each of the one or more partitions based on the orthogonal array corresponding to that partition. Each row of the active matrix specifies a level of each of the factors for testing the product characteristic at the associated partition. Hence, an active matrix specifies how a product characteristic can be tested at a partition. The implementation module 120 can coordinate with the processing facility 115 to test the product characteristic at each of the one or more partitions by conveying information related to the testing, such as the description of the product characteristic being tested, the factors being tested, and the levels for setting the factors as specified by one or more active matrices. In general, the implementation module 120 can communicate with any one of the modules 112, 114, 116 and 118 to obtain the pertinent information for testing a product characteristic.

The system 100 further includes a memory 160, which is configured to communicate with one or more of the modules 112, 114, 116, 118 or 120. For example, the memory 160 can be used to store the data (e.g., factors, levels and partitions) processed by the setup module 112, the level sets generated by the decomposition module 114 for the partitions, the orthogonal arrays generated by the orthogonal arrays generation module 116 for the partitions, the active matrices generated by the active matrix generation module 118 for the partitions, and/or instructions formulated by the implementation module 120 to direct the processing facility 115 to test a product characteristic at each partition.

Figure 2:
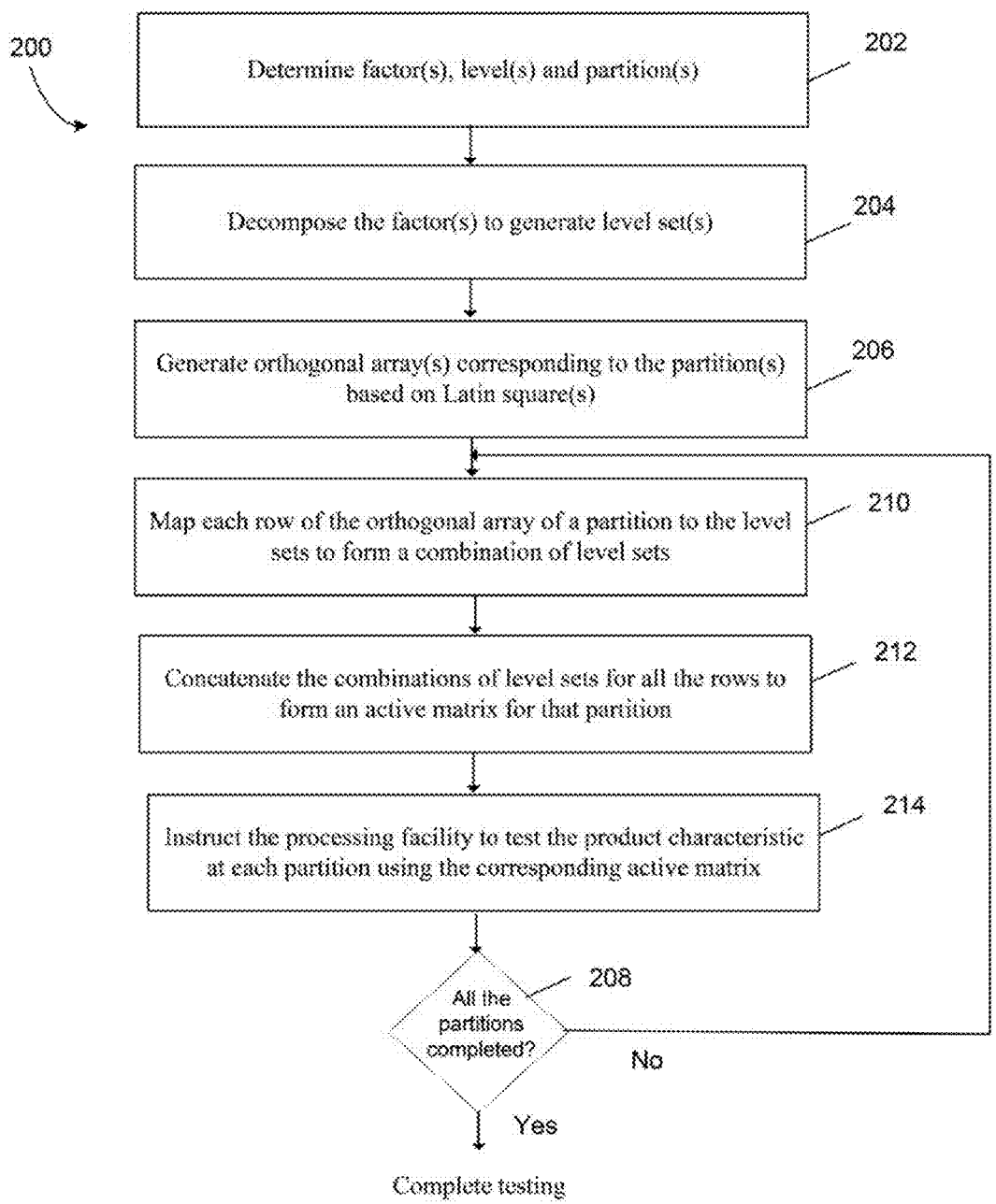
FIG. 2 shows an exemplary method for generating a design plan to test a product characteristic.

FIG. 2 shows an exemplary method 200 for generating a design plan to test a product characteristic. The elements of the method 200 are described using the exemplary system 100 of FIG. 1. Generating a design plan can include determining one or more factors, levels and/or partitions for testing a product characteristic (step 202), decomposing the factors to generate one or more level sets (step 204) and forming one or more orthogonal arrays for the partitions based on desirable properties of at least one Latin square matrix (step 206). For each partition, the method also includes mapping each row of the orthogonal array for the corresponding partition to the level sets to form a combination of the level sets (step 210) and concatenating the combinations of the level sets for all the rows of the orthogonal array to form an active matrix (step 212). The method 200 can instruct the processing facility 115 to test the product characteristic at each partition based on the active matrix (step 214). Steps 210, 212 and 214 can be iterated to generate an active matrix for each partition until all the partitions are processed (step 208). The combination of all the active matrices constitutes a design plan for testing the product characteristic.

At step 202, data received and processed by the system 100 (i.e., by the setup module 112 of the system 110) can include (i) a description of the product characteristic being tested, (ii) one or more factors supplied by a user to specify different parameters/variables for testing the product characteristic, (iii) one or more levels defining different settings (e.g., values) of each factor, and (iv) one or more partitions (e.g., points in time) for testing the product characteristic. A product characteristic can be any characteristic capable of being evaluated in association with a product, such as a feature of the product itself, a characteristic of a process used to develop the product, or a procedure related to the product. Multiple levels can be assigned to each factor, such as one, two, or more than two (i.e., multilevel). Each factor can be of a particular factor type including quantitative (e.g., a temperature factor with levels selected from the setting range of [a, b] or [a, b)), categorical (e.g., a machine number factor with levels selected from the setting range of $\{a_1, a_2, \ldots a_n\}$), discrete (e.g., a box size factor with levels selected from the setting range of $\{50, 150, 350\}$), or ordinal (e.g., a grade factor with levels selected from the setting range of $\{Good, Very Good, Much Very Good\}$). Hence, the method 200 of FIG. 2 can create design plans for factors of various types, not limited to numerical-based factors.

Hereinafter, a factor is denoted as $X_i^j$, where i denotes the ith factor and j denotes the number of levels assignable to that factor. In addition, the number of factors is denoted as n, the number of levels per ith factor is denoted as $L_i$, and the number of partitions is denoted as p. The total number of combinations or experimental runs (K) tested over the entire span of partitions can be expressed as $K=L_1*L_2 \ldots *L_n$. In addition, the number of combinations or experimental runs at each partition (m) is m=K/p. Therefore, instead of testing all K combinations of factor levels at each of the partitions, the system and method of the present technology can test the same number of combinations over all partitions, thus saving time and cost. In addition, the design plan created for each of the partitions has many desirable characteristics, including being orthogonal or nearly orthogonal and balanced. As a first example (Example 1), to test a product characteristic with 5 factors having a different number of levels per factor ($X_1^2$, $X_2^2$, $X_3^3$, $X_4^4$, and $X_5^7$), the total number of combinations is K=2*2*3*4*7=336, and the number of combinations tested per partition is m=112, if there are 3 partitions. Hence, instead of conducting 1008 (336*3) experimental runs over the span of all partitions according to a traditional approach, where all combinations are tested at each partition, the system and method of the present technology only need to conduct 336 experimental runs over the span of all partitions, which is a reduction of about 33%. As a second example (Example 2), to test a product characteristic with 3 factors and each factor can be assigned a different number of levels ($X_1^2$, $X_2^3$, $X_3^4$), the total number of combinations in this case is K=2*3*4=24, and the number of combinations tested per partition is m=12, if there are 2 partitions. This is a saving of 50% in comparison to the traditional approaches.

At step 204, the system 100 (i.e., the decomposition module 114) can decompose the levels specified for the factors into one or more level sets. At each partition, the system 100 can generate a level set for each factor, where each level set specifies one or more levels assignable to the corresponding factor at the corresponding partition. For example, the following algorithm can be used to generate a level set $A_j^L$ at the $i^{th}$ partition for a factor associated with L levels: $A_j^L=\{a_j|a_j=i+(j-1)*K, j\epsilon[1, L]\}$, $\forall i\epsilon[1,K]$, where i denotes the $i^{th}$ partition and K denotes the total number of partitions. FIG. 3 shows a table of level sets 300 generated for Example 1 and a table of level sets 350 generated for Example 2 using this algorithm. As shown, column 302 of table 300 corresponds to the factor $X_5^7$ of Example 1, where this factor can assume 7 possible levels that need to be partitioned into 3 different level sets. Hence, at the $1^{st}$ partition, the level set generated for this factor can be $\{1+(1-1)*3, 1+(2-1)*3, 1+(3-1)*3\}$ or $\{1, 4, 7\}$. Similar, at the $2^{nd}$ partition, the level generated for this factor can be $\{2+(1-1)*3, 2+(2-1)*3\}$ or $\{2, 5\}$. At the $3^{rd}$ partition, the level generated for this factor can be $\{3+(1-1)*3, 3+(2-1)*3\}$ or $\{3, 6\}$. In some cases, the level set generated for a factor at a partition is an empty set. For example, as shown in column 304 for the factor $X_1^2$, the level set produced at the $3^{rd}$ partition is an empty set because there is no element that can satisfy the given algorithm. In general, the purpose of including empty sets is to make a non-symmetrical design space symmetrical. Similarly, as shown in column 306 of the table 350 for Example 2, factor $X_3^4$ can assume 4 possible levels that need to be partitioned into 2 level sets. Hence, at the $1^{st}$ partition, the level set generated for this factor can be $\{1+(1-1)*2, 1+(2-1)*2\}$ or $\{1, 3\}$. At the $2^{nd}$ partition, the level set generated for this factor can be $\{2+(1-1)*2, 2+(2-1)*2\}$ or $\{2, 4\}$.

At step 206 of FIG. 2, the system 100 (i.e., the orthogonal arrays generation module 116) can generate an orthogonal array at each partition based on a corresponding Latin square matrix, where an element of each orthogonal array maps to a level set from the group of level sets produced for the factors (from step 204). Therefore, if there are p partitions, p orthogonal arrays are generated at step 206. An exemplary method for generating the orthogonal arrays are described below with reference to FIG. 7. Each orthogonal array can have $p^{(n-1)}$ rows and n columns, where p represents the number of the one or more partitions and n represents the number of the factors involved. Generally, each orthogonal array has p unique elements in n columns, and if any two arbitrary columns are chosen, all unique ordered 2-tuples (pairs) appear $p^{(n-3)}$ times. FIG. 4 shows two illustrative orthogonal arrays 402, 404 for Examples 1 and 2, respectively, at a particular partition. For Example 1 (p=3 and n=5), the orthogonal array generated for each partition is of size $3^{5-1}$ by 5 (or 81 by 5). For Example 2 (p=2 and n=3), the orthogonal array generated for each partition is of size $2^{3-1}$ by 3 (or 4 by 3). In Example 2, if any two columns of the matrix 404 is chosen, the possible pair-wise combinations of unique elements (i.e., (1,1), (1,2), (2,1) and (2,1)) appear exactly once.

In general, each column of an orthogonal array correlates to a unique factor and each element of the orthogonal array specifies a partition number, which when combined with the column index, correlates to a level set (produced at step 204). Each element of an orthogonal array can be an arbitrary number selected from [1, p]. With reference to Example 1, the element 402a of the orthogonal array 402, which has a value of 3 and is situated at column 3, is correlated to the level set of factor $X_3^3$ at the $3^{rd}$ partition (i.e., level set $\{3\}$ at element 308 of table 300). With reference to Example 2, the element 404a of the orthogonal array 404, which has a value of 1 and is situated at column 1, is correlated to the level set of factor $X_1^2$ for the $1^{st}$ partition (i.e., level set $\{1\}$ at element 310 of table 350). In some embodiments, rows in an orthogonal array containing an element that indexes to an empty set are removed to produce a reduced orthogonal array. As shown in the orthogonal array 402 of Example 1, row 3 of the matrix 402 includes element 402b, which has a value of 3 and is situated at column 2. Element 402b thus refers to the level set of factor $X_2^2$ at the $3^{rd}$ partition (i.e., an empty level set at element 312 of table 300). Therefore, the third row of the matrix 402 is eliminated. The same elimination process can be applied to all other rows in the orthogonal array that index to an empty level set.

Figure 5:
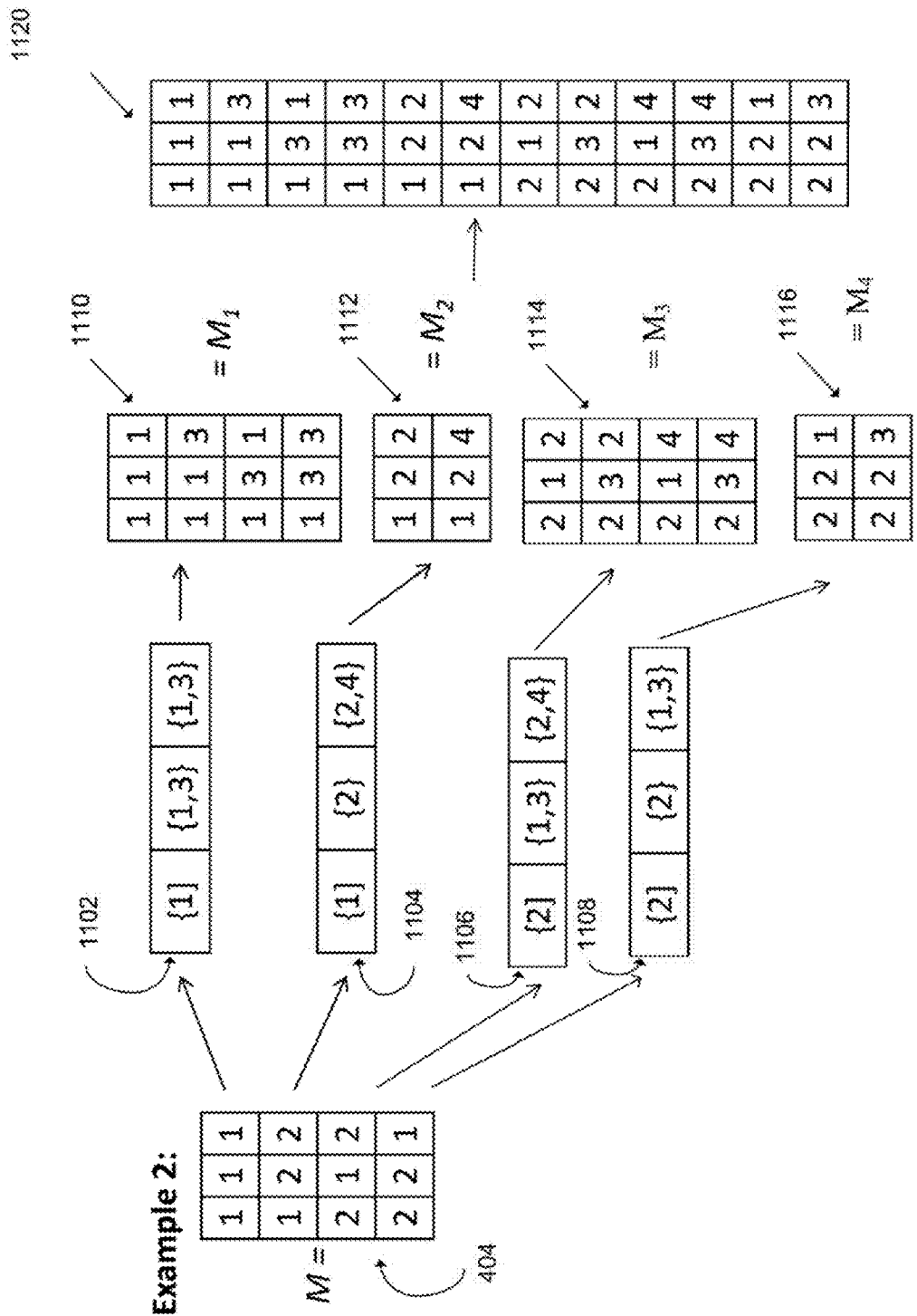
FIG. 5 shows exemplary combinations of level sets generated using the method of FIG. 2.

After the orthogonal arrays are created and suitably reduced (step 206), the system 100 (i.e., the active matrix generation module 118) can use the orthogonal arrays to generate an active matrix for each partition. Specifically, at step 210, the system can map each row of an orthogonal array to the level sets (from step 204) to form a combination of the level sets for a partition. As described above, each element of an orthogonal array, which is an arbitrary number between [1, p], can be used to select a level set. Furthermore, each row of an orthogonal array has n elements, which correlates to n level sets. Therefore, each row of an orthogonal array can specify a combination of n level sets. For instance, FIG. 4 shows the orthogonal array 404 of Example 2. Each row of the orthogonal array 404 can be used to select a combination of level sets, as shown in FIG. 5. Using row 1 of the orthogonal array 404 as an example, which consists of the elements [1, 1, 1], where the first element refers to the level set {1} for factor $X_1^2$ at partition 1, the second element refers to the level set {1, 3} for factor $X_2^3$ at partition 1, and the third element refers to the level set {1,3} for factor $X_3^4$ at partition 1. Hence, the first row of the orthogonal array 404 correlates to the combination 1102 consisting of the level sets {1}, {1, 3} and {1, 3}. Similarly, the second row of the orthogonal array 404 consists of the elements [1, 2, 2], where the first element refers to the level set {1} for factor $X_1^2$ at partition 1, the second element refers to the level set {2} for factor $X_2^3$ at partition 2, and the third element refers to the level set {2, 4} for factor $X_3^4$ at partition 2. Hence, the second row of the orthogonal array 404 correlates to the combination 1104 consisting of the level sets {1}, {2} and {2, 4}. The same method can be applied to other rows of the orthogonal array 404 to generate two additional combinations of level sets 1106 and 1108.

After a combination of level sets is determined from each row of an orthogonal array, all unique ordered permutations of elements drawn from each level set in that combination is formed as rows in a sub-active matrix. Hence, a sub-active matrix can have n columns and a number of rows equal to the number of unique ordered permutations possible. Using the level sets in the combination 1102 as an example, a sub-active matrix 1110 can be generated from the combination 1102 with each row containing a unique permutation of an element from each of the level sets. Because the three level sets in the combination 1102 has 1, 2, and 2 elements, respectively, the number of unique permutations is 4. Hence, the sub-active matrix 1110 has 4 rows. Using the level sets of the combination 1104 as another example, a sub-active matrix 1112 can be generated with each row containing a unique permutation of an element from each of the level sets. Because the three level sets in the combination 1104 has 1, 1, and 2 elements, respectively, the number of unique permutations is 2. Hence, the sub-active matrix 1112 has 2 rows. The same method can be applied to the two additional combinations of level sets 1106 and 1108 to generate two additional sub-active matrices 1114 and 1116, respectively.

With continued reference to FIG. 2, after the sub-active matrices are generated from an orthogonal array corresponding to a partition, the system 100 proceeds to concatenate all the sub-active matrices at step 212 to form a single active matrix for that partition. For example, the single active matrix can be formed by combining all the sub-active matrices row wise such that the resulting active matrix has n columns and a number of rows equal to the sum of the number of rows of the sub-active matrices. Each column of an active matrix corresponds to a factor. Each row of an active matrix corresponds to an experimental run. Hence, each row of the active matrix refer to a set of values to be assigned to their respective factors for testing a product characteristic in a trial run. In FIG. 5, an active matrix 1120 can be formulated for Example 2 by concatenating row-wise the sub-active matrices 1110, 1112, 1114 and 1116. The resulting active matrix 1120 thus has 12 rows (corresponding to 12 trial runs) and 3 columns (corresponding to 3 factors). Using the first row [1, 1, 1] of the active matrix 1120 as an example, this means that during a trial run at the corresponding partition, the first factor $X_1^2$ is set to its $1^{st}$ of two possible values, the second factor $X_2^3$ is set to its $1^{st}$ of three possible values, and the third factor $X_3^4$ is set to its $1^{st}$ of four possible values. Using the second row [1, 1, 3] of the active matrix 1120 as another example, this means that during another trial run of the same partition, the first factor $X_1^2$ is set to its first of two possible values, the second factor $X_2^3$ is set to its $1^{st}$ of three possible values, and the third factor $X_3^4$ is set to its $3^{rd}$ of four possible values.

Figure 6:
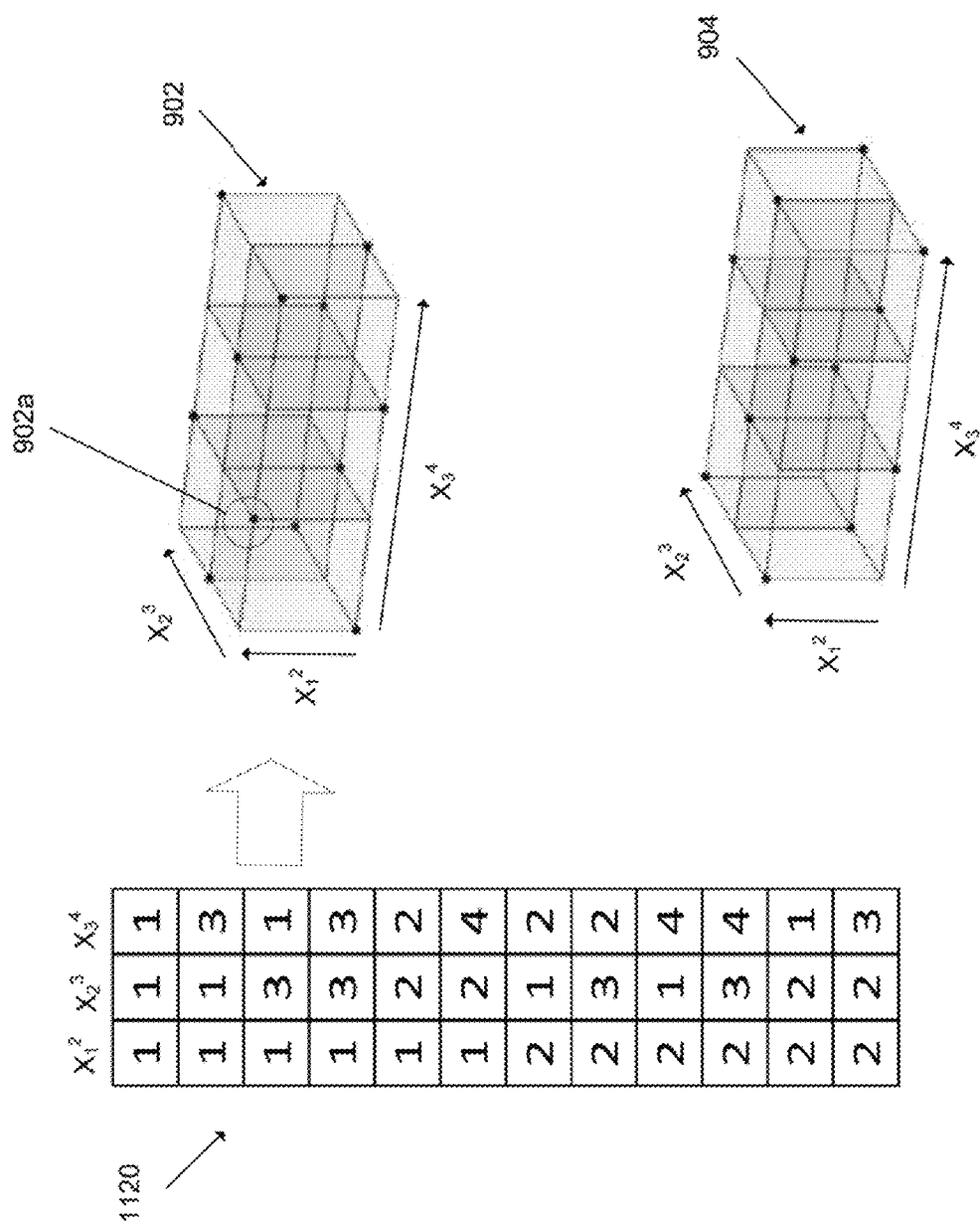
FIG. 6 shows exemplary active matrices generated using the method of FIG. 2.

FIG. 6 shows a visualization 902 of the active matrix 1120 produced for Example 2 at a single partition (e.g., at a first point in time). The visualization 902 represents a design space for the three factors $X_1^2$, $X_2^3$, and $X_3^4$. Each dot in the visualization 902 represents a particular point (i.e., a set of values assignable to the three factors) for testing the product characteristic at that partition. For example, the point 902a in the visualization 902 represents the set of values 2, 1, 2 assigned to the factors $X_1^2$, $X_2^3$, and $X_3^4$, respectively, which correlates to row 7 of the active matrix 1120. FIG. 6 also shows an exemplary visualization 904 of another active matrix (not shown) produced at a second partition (e.g., a second point in time). As shown, the second active matrix forms a design space for testing the product characteristic that is complementary to the design space of the first partition represented by the visualization 902. Thus, the second active matrix includes twelve rows, each corresponding to a point in the visualization 904. As illustrated by the active matrices of Example 2, instead of testing all possible combinations of the factor settings at each of the partitions, the system and method of the present technology can test the same number of combinations over all partitions, thus saving time and cost.

Generally, forming an active matrix at each partition using the method of FIG. 2 is advantageous because the resulting active matrix has many desirable properties including orthogonality or near orthogonality. Each active matrix can also be balanced. In addition, each active matrix can be symmetrical and/or min-max abeyant.

With reference to FIG. 2, after an active matrix for a partition is determined, the system 100 (i.e., the implementation module 120) can use the active matrix to the instruct the processing facility 115 to test the product characteristic at the corresponding partition (step 214). At step 208, if the system 100 determines that the product characteristic has been tested at every partition intended using an active matrix generated for that partition, the system 100 concludes the testing process. However, if there are still partitions at which testing has not been conducted, the system 100 generates a new active matrix corresponding to the untested partition (steps 210 and 212) and instructs the processing facility 115 to conduct the product characteristic testing at that partition using the associated active matrix (step 214). Hence, the steps 210, 212 and 214 can be repeated until the product characteristic is tested at every partition. In some embodiments, the testing results from a later partition can be used to validate results/predictions from an earlier partition. For example, if the partitions represent points in time, results can be collected from testing a product characteristic based on a first active matrix at time t. A model can be generated based on the testing results of time t, where the model forecasts the behavior of the product characteristic at one or more future points in time. At time t+1, results are collected again from testing the product characteristic based on a second active matrix. The results for time t+1 can be used to validate the forecasts made by the model at time t, such as checking whether outputs are indeed where they should be as forecasted. As another example, a model that is created at time t can be used to forecast the behavior of the product characteristic at multiple future points in time and, as time progresses and more test results are collected, the model can be updated on a periodic or continuous basis to improve its predictive ability.

Figure 7:
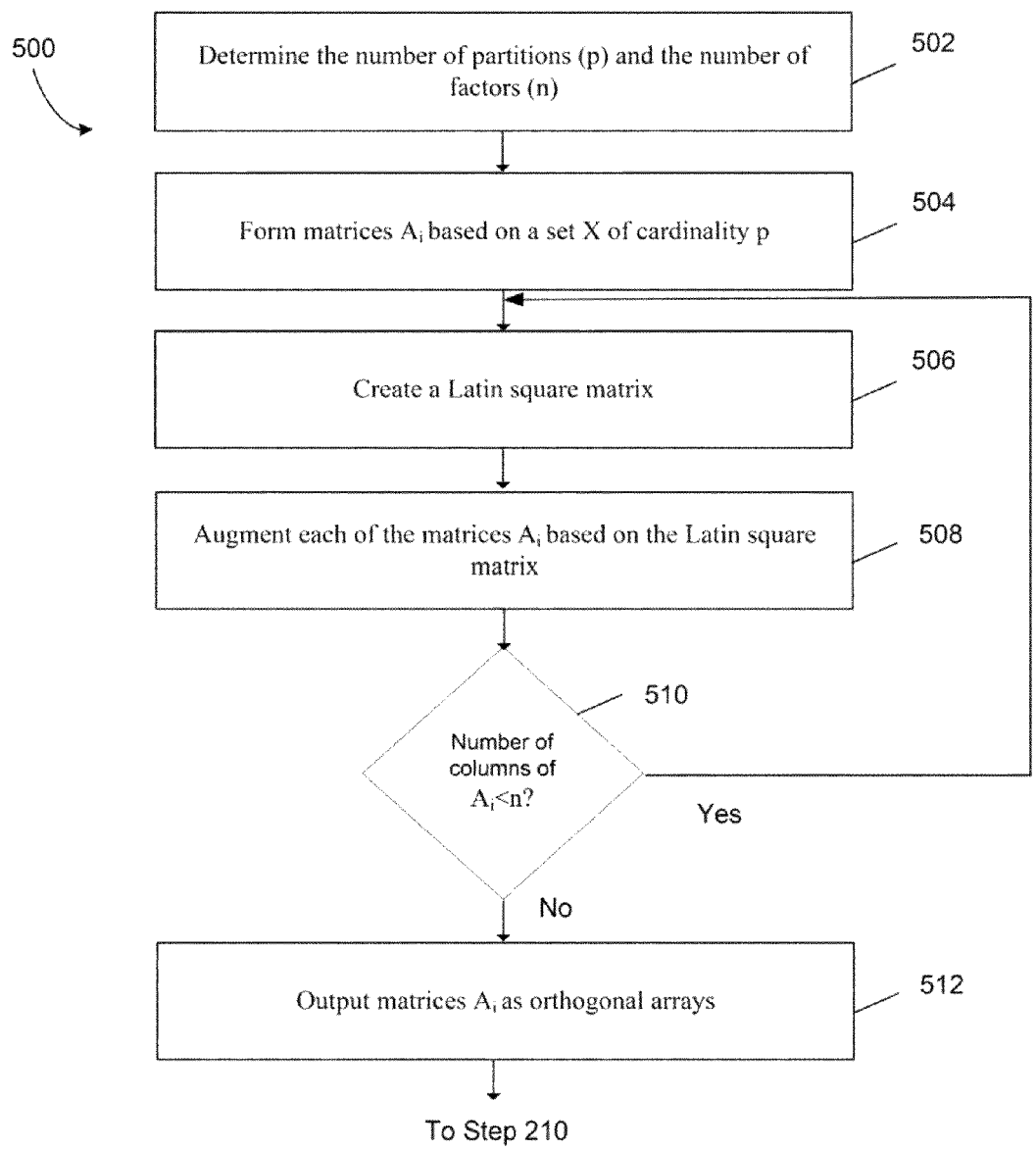
FIG. 7 shows an exemplary method for generating one or more orthogonal arrays, each corresponding to a partition.
Figure 8:
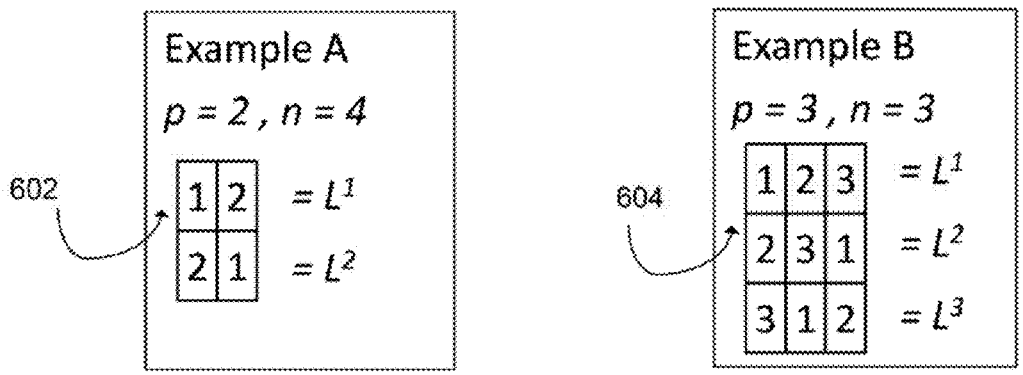
FIG. 8 shows exemplary Latin square matrices created by the method of FIG. 7 during a first iteration.
Figure 9:
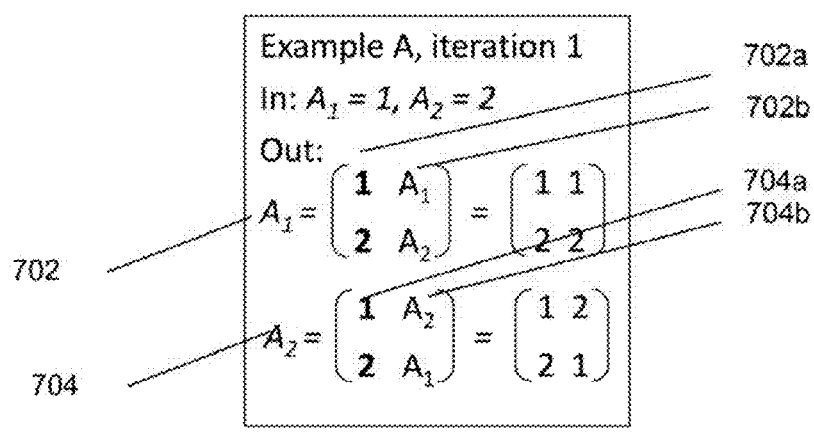
FIG. 9 shows exemplary $A_i$ matrices created by the method of FIG. 7 during a first iteration.
Figure 9:
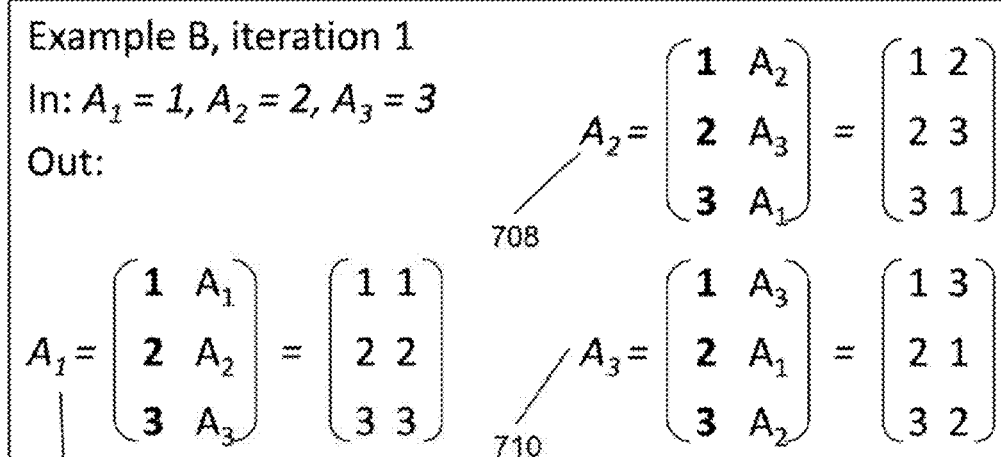

FIG. 7 shows an exemplary implementation 500 of step 206 for generating one or more orthogonal arrays for the partitions specified. At step 502, the system 100 obtains the number of partitions (p) and the number of factors (n) for testing a product characteristic. Such information can be specified by a user via the user interface 110 and the setup module 112. Generally, the goal of the method 500 is to create one or more orthogonal arrays, where the total number of orthogonal arrays created is equal to the number of partitions p. The size of each orthogonal array is $p^{(n-1)}$ rows by n columns. As a first example (Example A) described below with reference to FIGS. 8-11, given an experimental design with p=2 and n=4, each orthogonal array is of size $2^3$ by 4. As a second example (Example B) described below with reference to FIGS. 8, 9 and 12, given an experimental design with p=3 and n=3, each orthogonal array is of size $3^2$ by 3.

At step 504, multiple matrices $A_i$ are created based on a set X of cardinality p. The number of matrices $A_i$ created is equivalent to the number of partitions p. The set X can be generated using the algorithm $X=\{x_i|x_i=i, i\epsilon[1, p]\}$. Each matrix $A_i$ can be initially formed as a single element of X. Hence, each value of the set X is assigned to a matrix $A_i$, thereby generating p number of matrices. For Example A, X={1, 2} and matrices $A_1$=1 and $A_2$=2. For Example B, X={1, 2, 3} and matrices $A_1$=1, $A_2$=2 and $A_3$=3.

At step 506, a Latin square matrix L(p) if formed (of size p by p) based on the set X. In some embodiments, the Latin square matrix can be randomly generated. Each element in the Latin square matrix L(p) contains an element from X and each row and column in L(p) is a permutation of X. One approach for generating a Latin square matrix is to assign an ordered n-tuple from X and then assign a cyclic permutation of the first row to the p-1 remaining rows. FIG. 8 shows the Latin square matrices 602 and 604 created for Examples A and B, respectively, based on their respective sets X. In addition, each row of a Latin square matrix is denoted as $L^i$, where $i\epsilon[1, p]$.

At step 508, each of the matrices $A_i$ created at step 504 is augmented based on the Latin square matrix L(p) created at step 506. Specifically, the following algorithm can be used: for all matrices $A_i$, where $i\epsilon[1, p]$, and for all elements j in set X, where $j\epsilon[1, p]$, let $A_i^j=[X^j, A_y]$, where y=$L^i$(j). This means that for each matrix $A_i$, its first column is augmented by the set X. Its remaining columns are augmented by the other A matrices and permutated in an order according to a corresponding row $L^i$ of the Latin square matrix L(p). In some embodiments, the remaining columns of each matrix $A_i$ are augmented by the other A matrices and permutated in an order according to a corresponding column of the Latin square matrix L(p). FIG. 9 shows the $A_i$ matrices created for Examples A and B using this algorithm. Specifically, for Example A, the $A_1$ matrix 702 is augmented such that the set X={1, 2} is added to its first column 702a. Its remaining columns 702b are augmented by the $A_2$ matrix and arranged in an order according to $L^1$ of the Latin square matrix 602 of FIG. 8. Specifically, since $L^1$=[1, 2], the remaining columns 702b of the $A_1$ matrix 702 is arranged as [$A_1$, $A_2$].

Similarly, the $A_2$ matrix 704 is augmented such that the set X={1, 2} is added to its first column 704a. Its remaining columns 704b are augmented by the $A_1$ matrix and arranged in an order according to $L^2$ of the Latin square matrix 602 of FIG. 8. Specifically, since $L^2$=[2, 1], the remaining columns 704b of the $A_2$ matrix 704 is arranged as [$A_2$, $A_1$]. The same approach is used in Example B to augment the matrices $A_1$ 706, $A_2$ 708, and $A_3$ 710.

Figure 10:
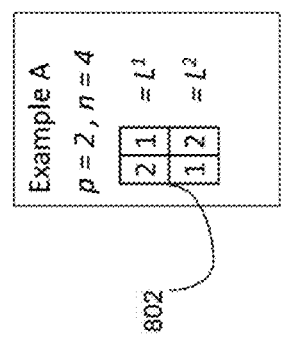
FIG. 10 shows a set of exemplary Latin square matrix and augmented $A_i$ matrices created by the method of FIG. 7 during a second iteration.
Figure 10:
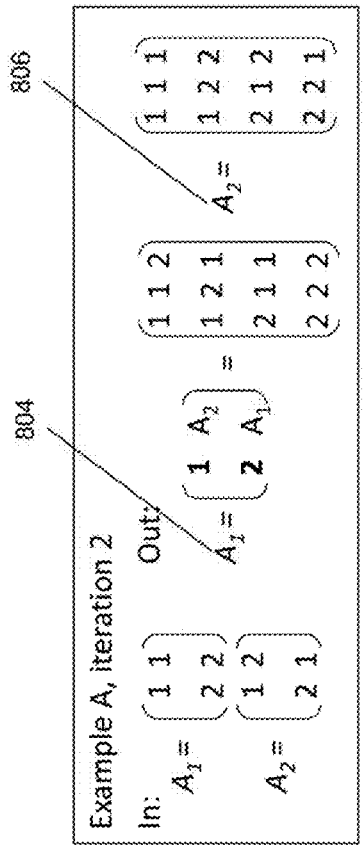
Figure 11:
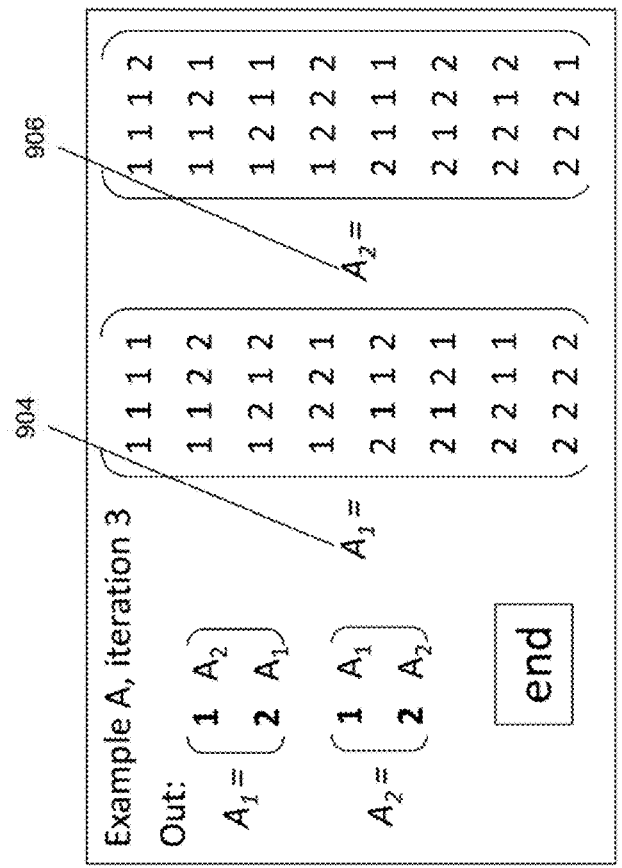
FIG. 11 shows a set of exemplary Latin square matrix and augmented $A_i$ matrices created by the method of FIG. 7 during a third iteration.

A determination is made at step 510 regarding whether the matrices $A_i$ have n columns. If these matrices have less than n columns, execution returns to steps 506 and 508 to iteratively augment the $A_i$ matrices until they have n columns. Once these matrices are sufficiently augmented, they can be returned to step 210 of FIG. 2 as the orthogonal arrays for the partitions. For instance, at the end of the first iteration for Example A, each of matrix $A_1$ 702 and matrix $A_2$ 704 has 2 columns, whereas n is 4 for Example A. Therefore, two more iterations are required to complete the orthogonal arrays of example A. With respect to Example A, FIG. 10 shows that a second iteration of the method 500 creates (1) an exemplary Latin square matrix 802 that can be randomly generated according to the approach described above for step 506; and (2) an $A_1$ matrix 804 augmented from the $A_1$ matrix 702 of the first iteration and an $A_2$ matrix 806 augmented from the $A_2$ matrix 704 of the first iteration according to the approach described above for step 508. FIG. 11 shows that a third iteration of the method 500 creates (1) an exemplary Latin square matrix 902 that can be randomly generated according to the approach described above for step 506; and (2) an $A_1$ matrix 904 augmented from the $A_1$ matrix 804 of the second iteration and an $A_2$ matrix 906 augmented from the $A_2$ matrix 806 of the second iteration according to the approach described above for step 508. At the end of the third iteration, both of the $A_1$ and $A_2$ matrices have n=4 columns. Therefore, the two matrices can be used as orthogonal arrays for the two partitions of Example A.

Similarly, at the end of the first iteration for Example B, each of matrices $A_1$ 706, $A_2$ 708, and $A_3$ 710 has 2 columns, whereas n is 3 for Example B. Therefore, one more iteration is needed to complete the orthogonal arrays of example B. With respect to Example B, FIG. 12 shows that a second iteration of the method 500 generates (1) an exemplary Latin square matrix 1002 that can be randomly generated according to the approach described above for step 506; and (2) an $A_1$ matrix 1004 augmented from the $A_1$ matrix 706 of the first iteration, an $A_2$ matrix 1006 augmented from the $A_2$ matrix 708 of the first iteration, and an $A_3$ matrix 1008 augmented from the $A_3$ matrix 710 of the first iteration that are generated according to the approach described above for step 508. At the end of the second iteration, the $A_1$, $A_2$ and $A_3$ matrices all have n=3 columns. Therefore, these matrices can be used as orthogonal arrays for the three partitions of Example B.

The design plan generation process of FIG. 2 can be used in various fields to perform product characteristic testing, including pharmaceutical, marketing and manufacturing fields. For example, the process of FIG. 2 can be used to determine a design plan for testing the stability of a pharmaceutical formulation, where the factors represent parameters for testing the pharmaceutical formulation with respect to the stability evaluation. The testing is conducted over multiple partitions that represent points in time selected from within a range of 0 to 36 months. The factors can include one or more of an API concentration, a pH level, a methionine concentration, or a temperature level. The API concentration factor can be assigned one or more levels selected from a range of 15 to 20 mg/ml. The pH factor can be assigned one or more levels from within a range of 5.5 to 6.5. The methionine concentration factor can be assigned one or more levels from within a range of 5 to 15 mM. The temperature factor can be assigned one or more levels from within a range of 5 to 25 C.

As another example, the process of FIG. 2 can be used to determine a design plan for testing customer response to a sensor used to measure and control indoor climate that is developed by a company. As part of its campaign to develop new and better sensors, the company can determine market response by varying five features/attributes associated with the sensor. These attributes include: $x_1$ (price), $x_2$ (status indicator indicating whether the sensor is in operating mode or not), $x_3$ (logo type affixed to the sensor), $x_4$ (control screens, which can be made in either a digital or analog mode), and $x_5$ (product design, which can be tested with respect to four different design shapes rectangular, square, circular, and beveled). For the survey, 32 respondents are asked about their opinions with respect to these factors, and they expressed their judgment as a rating ranging from 1-9. The respondent pool can include seven users ($A_1$-$A_7$), seven consultants ($K_1$-$K_7$), twelve company employees ($T_1$-$T_{12}$) and six house owners ($F_1$-$F_6$).

In yet another example, the general process of FIG. 2 can be used to determine a design plan for testing the effect of different granulators on the properties of granules and tablets. In this case, the factors represent parameters that affect granulation. The factors can include one or more of the following: equipment used, impeller speed, wet massing time and amount of water added. The equipment factor can be assigned three possible levels—Mixer Torque Rheometer (MTR), Mi-Pro, or Diosna. The impeller speed factor can be assigned three possible levels—50 rpm, 75 rpm, or 100 rpm. The wet massing time factor can be assigned three possible levels—1 minute, 5 minutes, or 10 minutes. The amount water added factor can be assigned three possible levels—0.35, 0.50, 0.65, or 0.8 ml/g.

In yet another example, the process of FIG. 2 can be used to determine a plan for testing the robustness of an automotive suspension design. Specifically, the purpose of the testing is to minimize the peak force on the strut while driving on rough surfaces by finding the best combination of seven factors including Jounce bumper length (JBL), jounce bumper length entry stiffness (JBES), compression damping (CD), extension damping (ED), spring rate (SR), jounce travel (JT) and rebound travel (RT). The JBL factor can be assigned a base value, a level 30 mm above the base value, and a level 30 mm below the based value. The JBES factor can be assigned levels including 100%, 300% and 33%. The CD factor can be assigned one level 719. The ED factor can be assigned three levels 400, 1600 and 100. The SR factor can be assigned three levels 100%, 120% and 80%. The JT factor can be assigned three levels 100%, 117% and 83%. The RT factor can be assigned three levels 100%, 122% and 78%.

The above-described techniques can be implemented in digital electronic circuitry, or in computer hardware, firmware, software, or in combinations of them. The implementation can be as a computer program product, e.g., a computer program tangibly embodied in an information carrier, e.g., in a machine-readable storage device, for execution by, or to control the operation of, data processing apparatus, e.g., a programmable processor, a computer, or multiple computers. A computer program can be written in any form of programming language, including compiled or interpreted languages, and it can be deployed in any form, including as a stand-alone program or as a module, component, subroutine, or other unit suitable for use in a computing environment. A computer program can be deployed to be executed on one computer or on multiple computers at one site or distributed across multiple sites and interconnected by a communication network.

Method steps can be performed by one or more programmable processors executing a computer program to perform functions of the technology by operating on input data and generating output. Method steps can also be performed by, and apparatus can be implemented as, special purpose logic circuitry, e.g., an FPGA (field programmable gate array) or an ASIC (application-specific integrated circuit). Modules can refer to portions of the computer program and/or the processor/special circuitry that implements that functionality.

Processors suitable for the execution of a computer program include, by way of example, both general and special purpose microprocessors, and any one or more processors of any kind of digital computer. Generally, a processor receives instructions and data from a read-only memory or a random access memory or both. The essential elements of a computer are a processor for executing instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. Data transmission and instructions can also occur over a communications network. Information carriers suitable for embodying computer program instructions and data include all forms of non-volatile memory, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in special purpose logic circuitry.

The terms "module" and "function," as used herein, mean, but are not limited to, a software or hardware component which performs certain tasks. A module may advantageously be configured to reside on addressable storage medium and configured to execute on one or more processors. A module may be fully or partially implemented with a general purpose integrated circuit ("IC"), FPGA, or ASIC. Thus, a module may include, by way of example, components, such as software components, object-oriented software components, class components and task components, processes, functions, attributes, procedures, subroutines, segments of program code, drivers, firmware, microcode, circuitry, data, databases, data structures, tables, arrays, and variables. The functionality provided for in the components and modules may be combined into fewer components and modules or further separated into additional components and modules. Additionally, the components and modules may advantageously be implemented on many different platforms, including computers, computer servers, data communications infrastructure equipment such as application-enabled switches or routers, or telecommunications infrastructure equipment, such as public or private telephone switches or private branch exchanges ("PBX"). In any of these cases, implementation may be achieved either by writing applications that are native to the chosen platform, or by interfacing the platform to one or more external application engines.

To provide for interaction with a user, the above described techniques can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer (e.g., interact with a user interface element). Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input.

The above described techniques can be implemented in a distributed computing system that includes a back-end component, e.g., as a data server, and/or a middleware component, e.g., an application server, and/or a front-end component, e.g., a client computer having a graphical user interface and/or a Web browser through which a user can interact with an example implementation, or any combination of such back-end, middleware, or front-end components. The components of the system can be interconnected by any form or medium of digital data communications, e.g., a communications network. Examples of communications networks, also referred to as communications channels, include a local area network ("LAN") and a wide area network ("WAN"), e.g., the Internet, and include both wired and wireless networks. In some examples, communications networks can feature virtual networks or sub-networks such as a virtual local area network ("VLAN"). Unless clearly indicated otherwise, communications networks can also include all or a portion of the PSTN, for example, a portion owned by a specific carrier.

The computing system can include clients and servers. A client and server are generally remote from each other and typically interact through a communications network. The relationship of client and server arises by virtue of computer programs running on the respective computers and having a client-server relationship to each other.

Various embodiments are depicted as in communication or connected by one or more communication paths. A communication path is not limited to a particular medium of transferring data. Information can be transmitted over a communication path using electrical, optical, acoustical, physical, thermal signals, or any combination thereof. A communication path can include multiple communication channels, for example, multiplexed channels of the same or varying capacities for data flow.

Multiple user inputs can be used to configure parameters of the depicted user interface features. Examples of such inputs include buttons, radio buttons, icons, check boxes, combo boxes, menus, text boxes, tooltips, toggle switches, buttons, scroll bars, toolbars, status bars, windows, or other suitable icons or widgets associated with user interfaces for allowing a user to communicate with and/or provide data to any of the modules or systems described herein.

While the invention has been particularly shown and described with reference to specific embodiments, it should be understood by those skilled in the art that various changes in form and detail may be made therein without departing from the spirit and scope of the invention as defined by the appended claims. For example, a person of ordinary skill in the art understands that rows and columns of matrices can be consistently transposed during calculation to derive the same results. For instance, even though each column of an active matrix is explained above to correlate to a factor and each row to correlate to an experimental run, the same matrix can be transposed such that each row correlates to a factor and each column correlates to an experimental run while still conveying the same information for a design plan.

The invention claimed is:

1. A computer-implemented method for causing testing of a product characteristic in a processing facility, the method comprising:
determining, by a computing device, (i) a plurality of factors corresponding to different parameters for testing the product characteristic, (ii) a plurality of levels corresponding to different settings of each factor, and (iii) one or more partitions for testing the product characteristic;
decomposing, by the computing device, the plurality of factors to generate a plurality of level sets, wherein each level set comprises zero or more levels assignable to each factor at each partition;
generating, by the computing device, a plurality of orthogonal arrays by distributing elements of each matrix using at least one Latin square matrix, wherein (i) each orthogonal array corresponds to a partition and (ii) an element of each orthogonal array indexes a level set from the plurality of level sets produced from the decomposition;
performing, by the computing device, at each of the partitions, steps comprising:
mapping each row of the corresponding orthogonal array to the plurality level sets to form a combination of level sets, wherein each row of the orthogonal array determines the formation of the combination by specifying the level sets to combine; and
concatenating the plurality of combinations of level sets generated from the rows of the orthogonal array to form an active matrix, wherein each row of the active matrix specifies a level of each of the plurality of factors for testing the product characteristic at the corresponding partition; and
causing, by the computing device, testing of the product characteristic in the processing facility that adjusts, at each one of the one or more partitions, the different parameters using the levels specified by the corresponding active matrix.

2. The computer-implemented method of claim 1, wherein the one or more partitions comprise a plurality of points in time for testing the product characteristic.

3. The computer-implemented method of claim 1, wherein each factor is associated with a type comprising one of a quantitative, categorical, discrete or ordinal type.

4. The computer-implemented method of claim 1, wherein each orthogonal array has a size of $p^{n-1}$ by n, wherein p represents the number of the one or more partitions and n represents the number of the plurality of factors.

5. The computer-implemented method of claim 1, further comprising reducing each orthogonal array if a level set is an empty set with no elements.

6. The computer-implemented method of claim 5, wherein reducing the orthogonal array comprises removing each row in the orthogonal array that includes an element indexing to an empty set of the plurality of level sets.

7. The computer-implemented method of claim 1, wherein the active matrices for the one or more partitions cover all combinations of the plurality of levels for the plurality of factors.

8. The computer-implemented method of claim 1, wherein each active matrix achieves orthogonality and balance.

9. The computer-implemented method of claim 1, wherein the Latin square matrix is random.

10. The computer-implemented method of claim 1, wherein generating the orthogonal arrays at the one or more partitions comprises:
  a. determining the number of the one or more partitions (p) and the number of the plurality of factors (n);
  b. forming a plurality of matrices $A_i$ based on a set X of cardinality p, wherein i $\in[1,p]$;
  c. creating a Latin square matrix of size p by p;
  d. augmenting each of the plurality of matrices $A_i$ based on the Latin square matrix; and
  e. repeating steps c to d if the number of columns of each of the plurality of matrices $A_i$ is less than n, wherein each of the plurality of matrices $A_i$ represents an orthogonal array.

11. The computer-implemented method of claim 1, wherein the product characteristic represents a metric related to a pharmaceutical formulation and the plurality of factors represent parameters for testing the pharmaceutical formulation with respect to the metric.

12. The computer-implemented method of claim 11, wherein the metric comprises stability of the pharmaceutical formulation.

13. The computer-implemented method of claim 11, where the plurality of factors comprise one or more of an active pharmaceutical ingredient (API) concentration, a pH level, a methionine concentration, or a temperature level.

14. The computer-implemented method of claim 13, further comprising selecting the plurality of levels for (i) the API concentration from within a range of 15 to 20 mg/ml, (ii) the pH level from within a range of 5.5 to 6.5, (iii) the methionine concentration from within a range of 5 to 15 mM, and (iv) the temperature level from within a range of 5 to 25 C.

15. The computer-implemented method of claim 11, wherein the one or more partitions comprise a plurality of points in time selected from within a range of 0 to 36 months.

16. The computer-implemented method of claim 1, wherein the product characteristic comprises a product feature, a process or a procedure.

17. The computer-implemented method of claim 1, wherein each active matrix comprises one of an orthogonal or nearly orthogonal matrix.

18. A computer-implemented system for causing testing of a product characteristic in a processing facility, the system comprising:
  a setup module for determining (i) a plurality of factors corresponding to different parameters for testing the product characteristic, (ii) a plurality of levels corresponding to different settings of each factor, and (iii) one or more partitions for testing the product characteristic;
  a decomposition module for decomposing the plurality of factors to generate a plurality of level sets, wherein each level set comprises zero or more levels assignable to each factor at each partition;
  an orthogonal arrays generation module for generating a plurality of orthogonal arrays by distributing elements of each matrix using at least one Latin square matrix, wherein (i) each orthogonal array corresponds to a partition and (ii) an element of each orthogonal array indexes a level set from the plurality of level sets produced by the decomposition module;
  an active matrix generation module for generating an active matrix at each of the one or more partitions by:
    mapping each row of the corresponding orthogonal array to the plurality level sets to form a combination of level sets, wherein each row of the orthogonal array determines the formation of the combination by specifying the level sets to combine; and
    concatenating the plurality of combinations of level sets generated from the rows of the orthogonal array to form the active matrix, wherein each row of the active matrix specifies a level of each of the plurality of factors for testing the product characteristic at the corresponding partition; and
  an implementation module for causing testing of the product characteristic in the processing facility that adjusts, at each of the one or more partitions, the different parameters using the levels specified by the corresponding active matrix.

19. The computer-implemented system of claim 18, wherein each orthogonal array has a size of $p^{n-1}$ by n, wherein p represents the number of the one or more partitions and n represents the number of the plurality of factors.

20. The computer-implemented system of claim 18, wherein the orthogonal arrays generation module is further configured to reduce each orthogonal array if a level set is an empty set.

21. The computer-implemented system of claim 18, wherein the product characteristic represents a metric related to a pharmaceutical formulation and the plurality of factors represent variables for testing the pharmaceutical formulation with respect to the metric.

22. The computer-implemented system of claim 21, wherein the metric comprises stability of the pharmaceutical formulation.

23. The computer-implemented system of claim 18, wherein the orthogonal arrays generation module produces the plurality of orthogonal arrays by:
  a. determining the number of the one or more partitions (p) and the number of the plurality of factors (n);
  b. forming a plurality of matrices $A_i$ based on a set X of cardinality p, wherein i $\in[1,p]$;
  c. creating a Latin square matrix of size p by p;
  d. augmenting each of the plurality of matrices $A_i$ based on the Latin square matrix; and
  e. repeating steps c to d if the number of columns of each of the plurality of matrices $A_i$ is less than n, wherein each of the plurality of matrices $A_i$ represents an orthogonal array.

24. The computer-implemented method of claim 1, wherein the product characteristic comprises stability of a pharmaceutical formulation, and wherein causing testing of the product characteristic in the processing facility comprises causing adjustment, at each one of the one or more partitions, the different parameters comprising at least one of an active pharmaceutical ingredient (API) concentration, a pH level, a methionine concentration, or a temperature level.

25. The computer-implemented system of claim 1, wherein the product characteristic comprises stability of a pharmaceutical formulation, and wherein the implementation module is configured to cause testing of the product characteristic in the processing facility that adjusts, at each one of the one or more partitions, the different parameters comprising at least one of an active pharmaceutical ingredient (API) concentration, a pH level, a methionine concentration, or a temperature level.

* * * * *